United States Patent [19]

Barcel et al.

[11] Patent Number: 5,267,564

[45] Date of Patent: Dec. 7, 1993

[54] PACEMAKER LEAD FOR SENSING A PHYSIOLOGIC PARAMETER OF THE BODY

[75] Inventors: James E. Barcel, Simi Valley; Alvin H. Weinberg, Moorpark; Shahram Moaddeb, Woodland Hills, all of Calif.; James R. Thacker, Lake Jackson, Tex.

[73] Assignee: Siemens Pacesetter, Inc., Sylmar, Calif.

[21] Appl. No.: 716,032

[22] Filed: Jun. 14, 1991

[51] Int. Cl.$^5$ .................................... A61B 5/0205
[52] U.S. Cl. ........................ 128/634; 607/22; 607/122
[58] Field of Search ............... 128/634, 637, 700, 789, 128/786, 419 P, 419 PG; 606/12, 14

[56] References Cited

U.S. PATENT DOCUMENTS

| | | | |
|---|---|---|---|
| 3,123,066 | 3/1964 | Brumley | 128/2 |
| 3,461,856 | 8/1969 | Polanyi | 128/2 |
| 4,202,339 | 5/1980 | Wirtzfeld et al. | 128/419 PG |
| 4,467,807 | 8/1984 | Bornzin | 128/419 PG |
| 4,727,879 | 3/1988 | Liess et al. | 128/633 |
| 4,791,935 | 12/1988 | Baudino et al. | 128/637 |
| 4,807,629 | 2/1989 | Baudino et al. | 128/419 PG |
| 4,813,421 | 3/1989 | Baudino et al. | 128/633 |
| 4,815,469 | 3/1989 | Cohen et al. | 128/634 |
| 4,903,701 | 2/1990 | Moore et al. | 128/419 PG |
| 4,967,755 | 11/1990 | Pohndorf | 128/786 |

Primary Examiner—Lee S. Cohen
Assistant Examiner—Brian L. Casler
Attorney, Agent, or Firm—Lisa P. Weinberg

[57] ABSTRACT

The present invention includes a body implantable lead having a multi-polar proximal connector, at least a first conductor coupled to at least one stimulating electrode, a sensor for sensing at least one physiologic parameter of the body, and a second and a third conductor coupled to the sensor. The sensor is hermetically sealed in a D-shaped housing. Sensor components are mounted onto a microelectronic substrate which is advantageously placed on an inner flat portion of the D-shaped housing. End caps having glass frit sealing rings are used to seal the ends of the shell. A hermetic seal is easily achieved by heating the glass frit such that the glass frit reflows between the end caps and the shell. Advantageously, the sensor terminals are sized to fit snugly within a narrow bore of the end cap which is then welded closed. The D-shaped sensor is placed on a carrier having at least two lumens. At least the first and second conductors pass through the lumens for connection with the stimulating electrode and the distal end of the sensor. Advantageously, the D-shaped housing reduces the area that needs to be hermetically sealed by more than half, and thus reduces the overall diameter of the lead. Advantageously, the conductors coupled to the sensor function independently from the stimulation conductors so that interference with basic operation of the pacemaker is prevented.

5 Claims, 9 Drawing Sheets

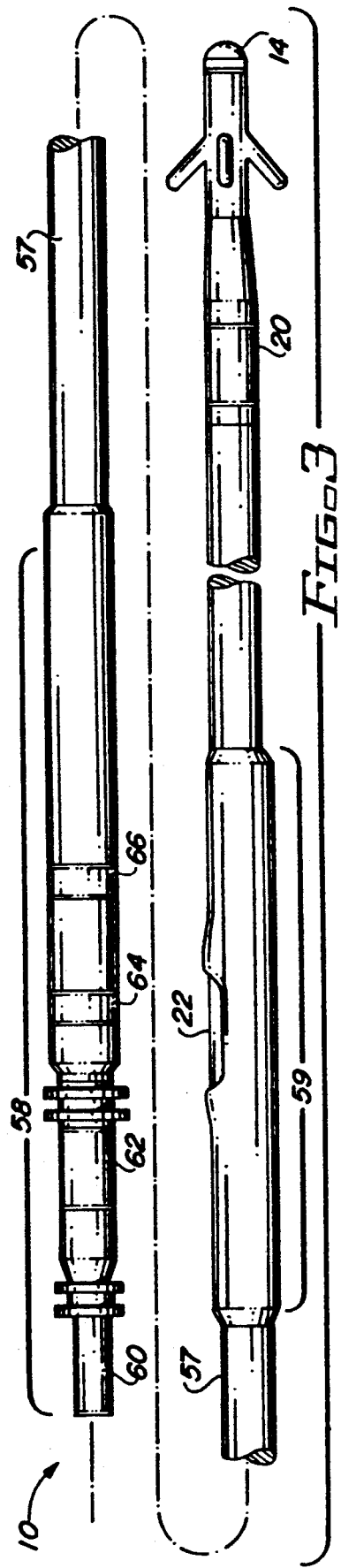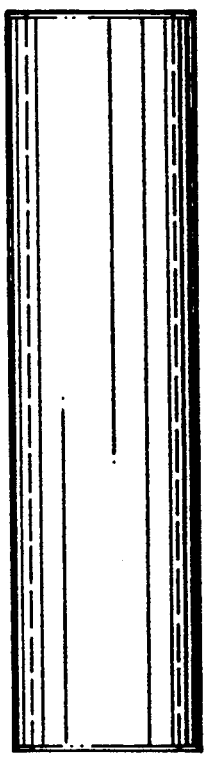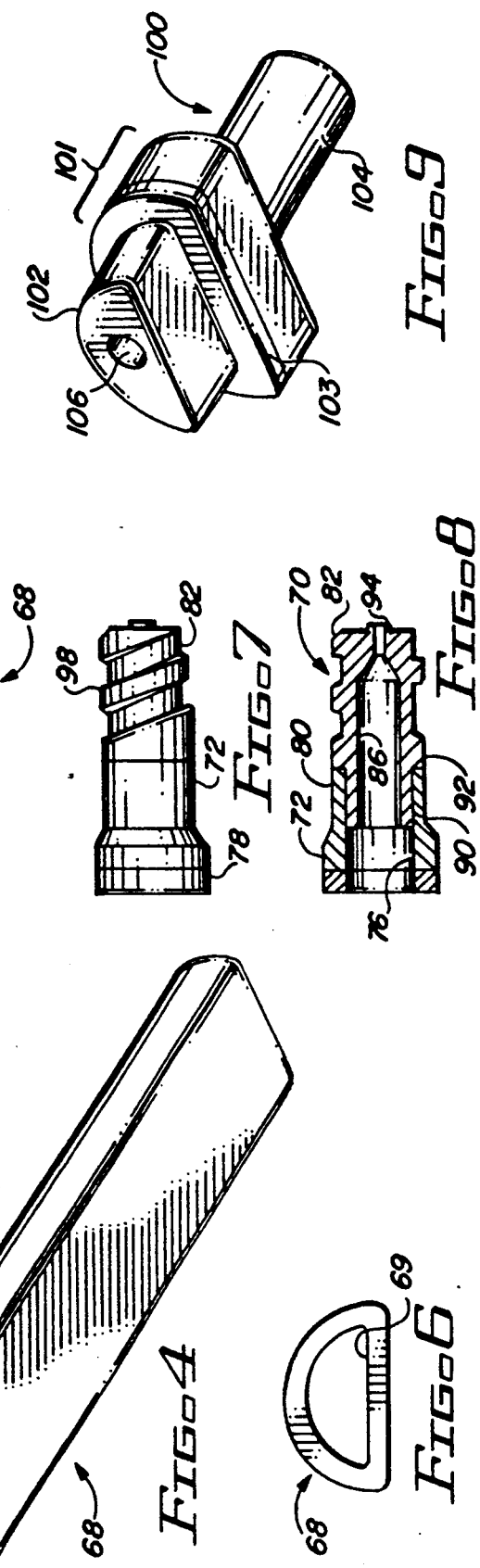

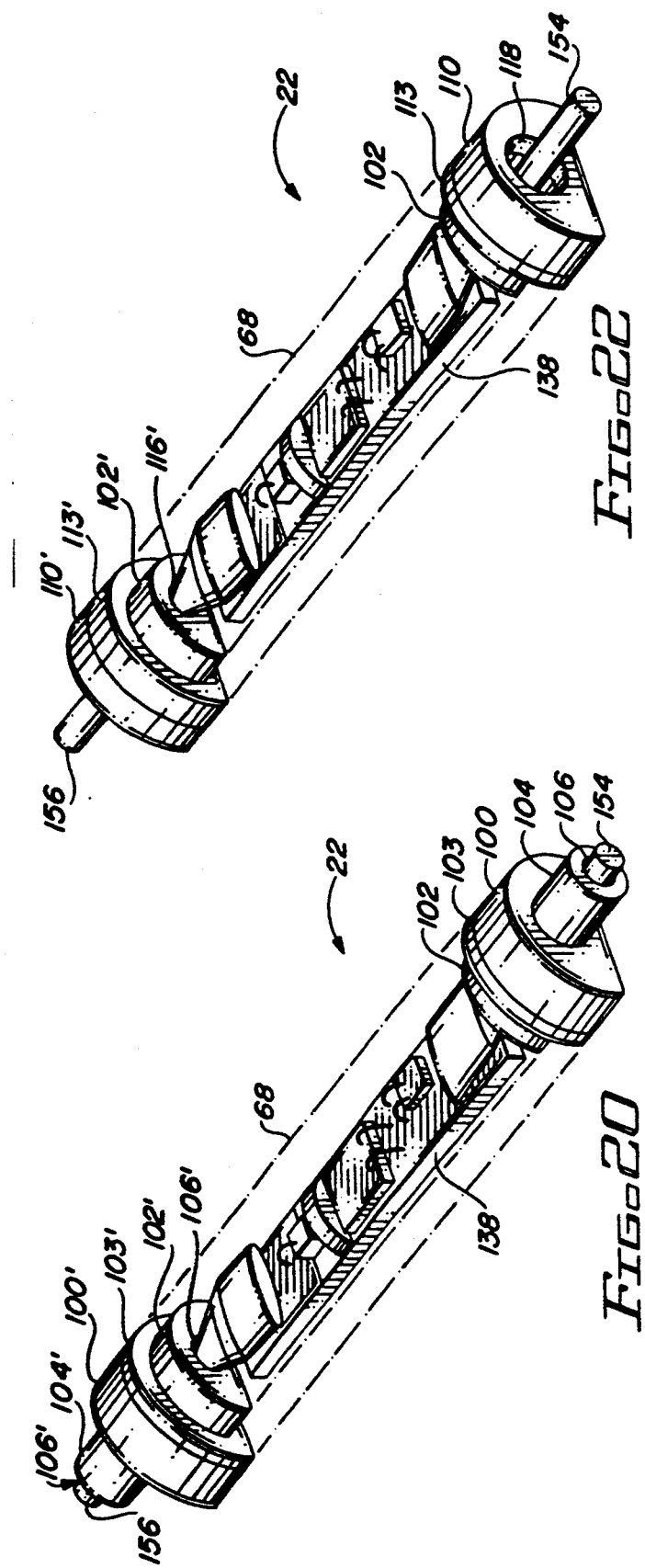
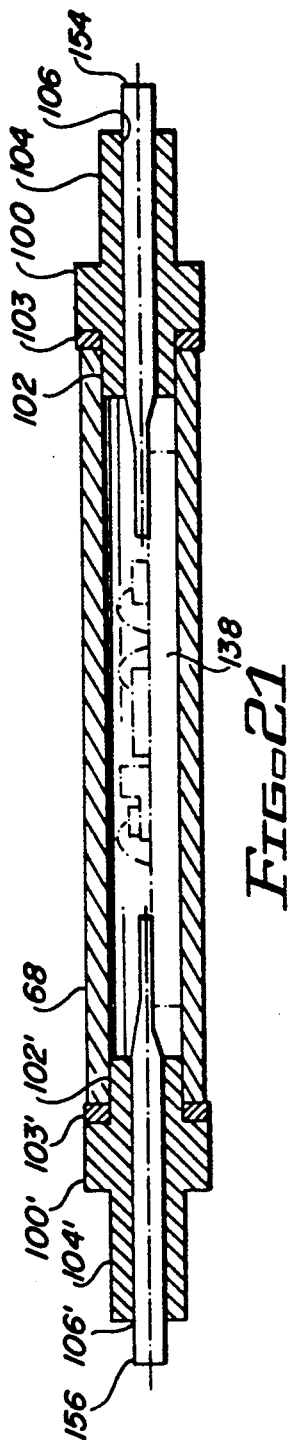

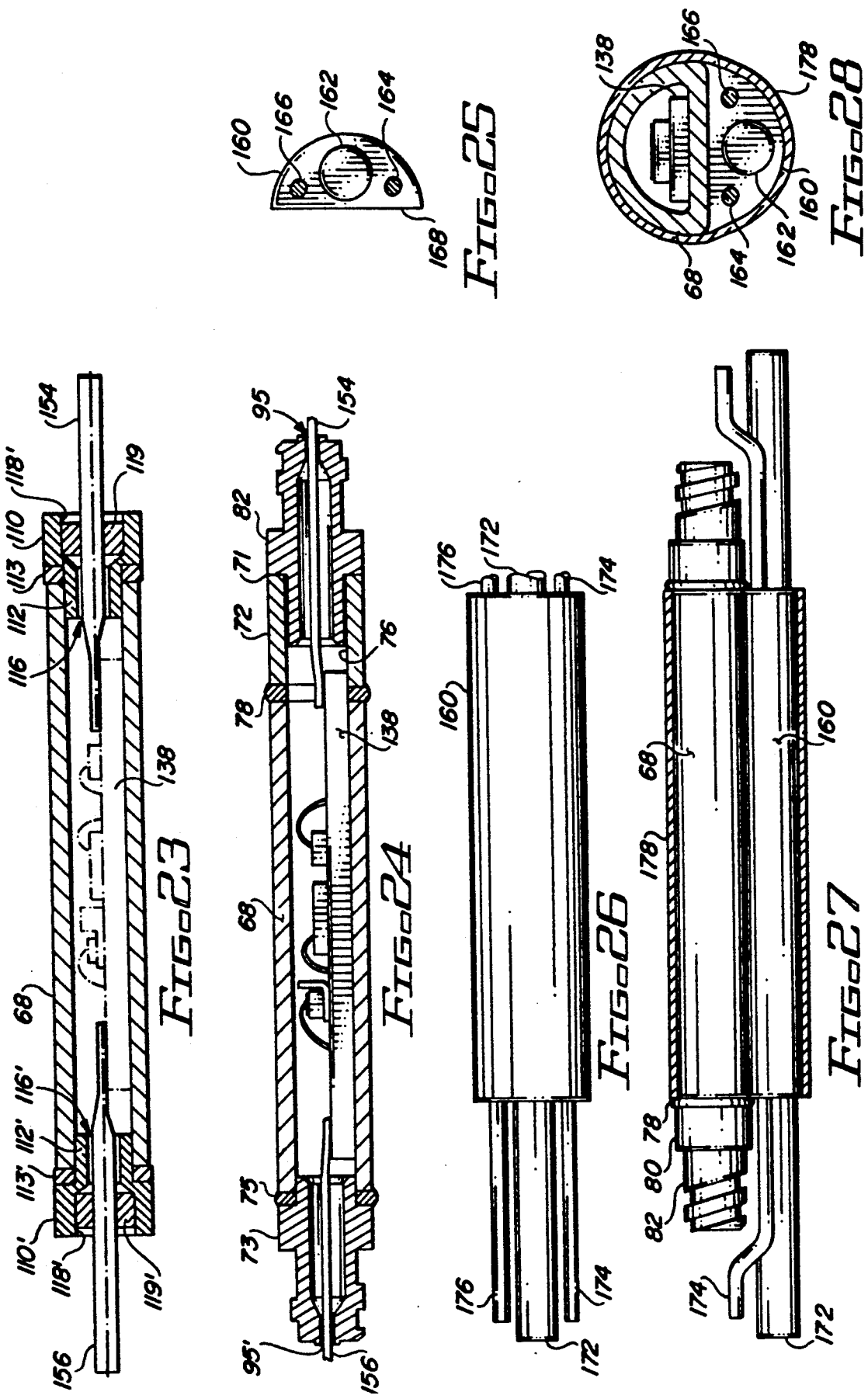

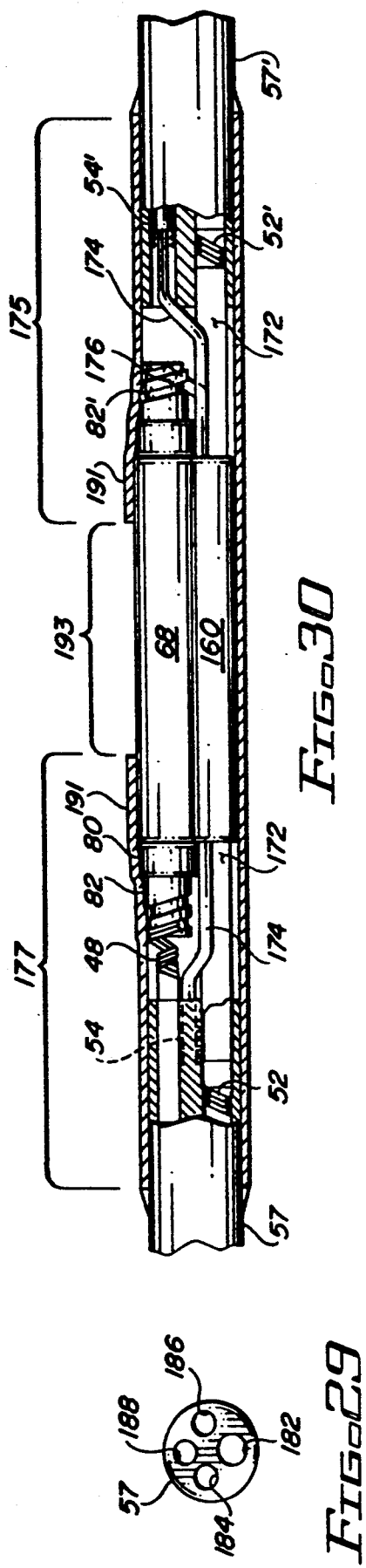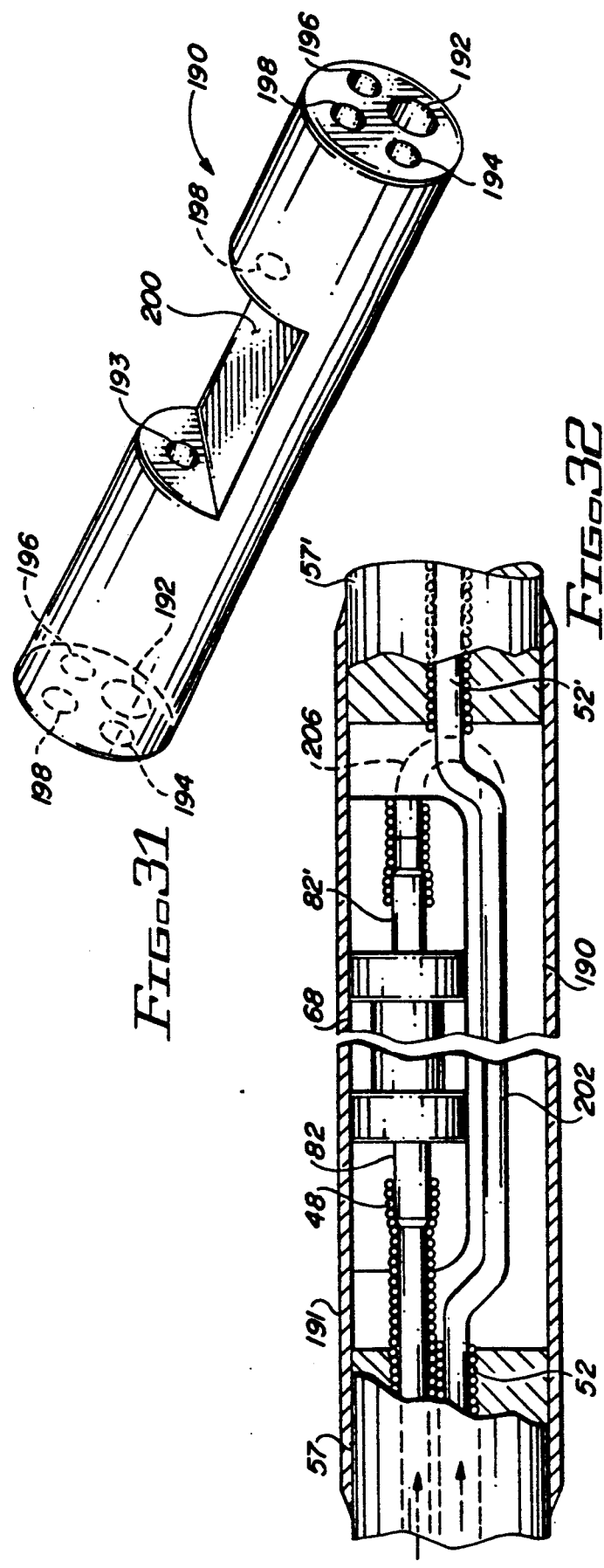

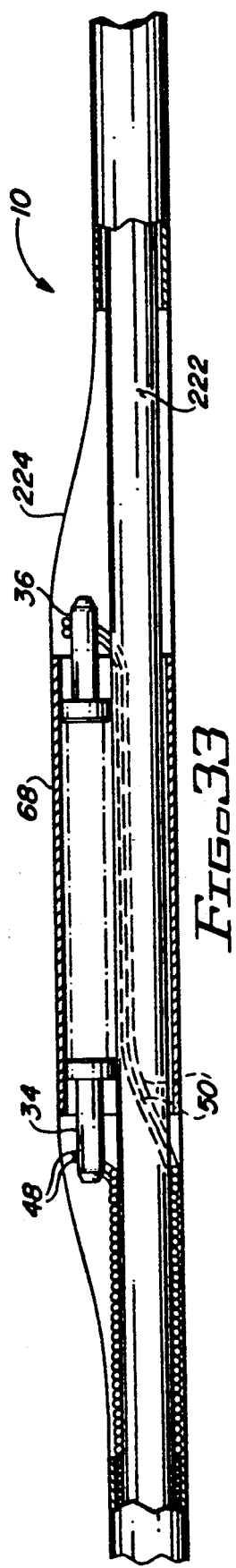
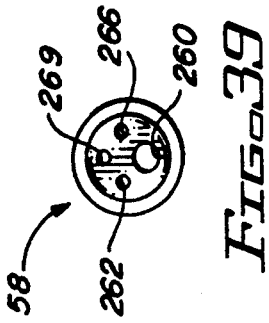
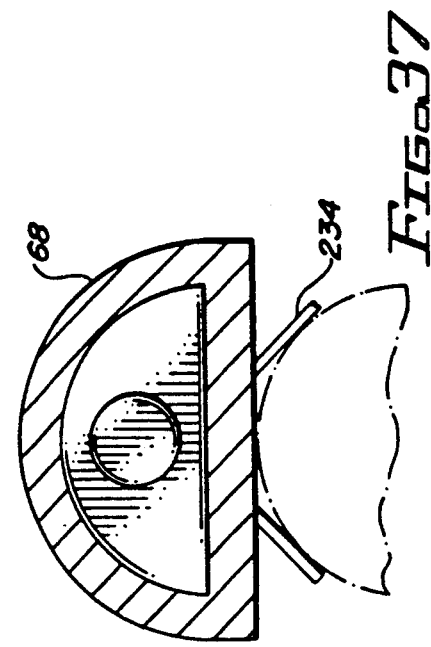
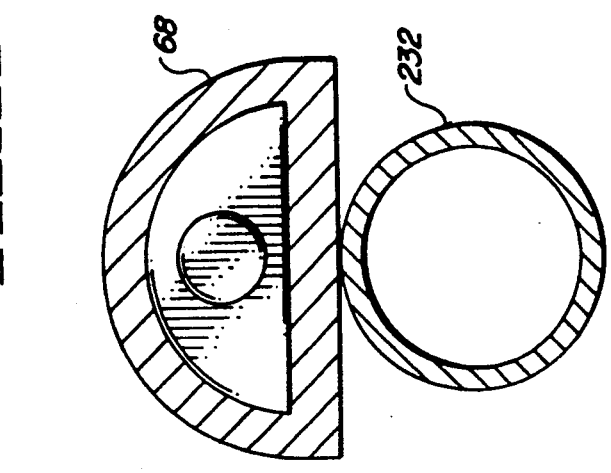
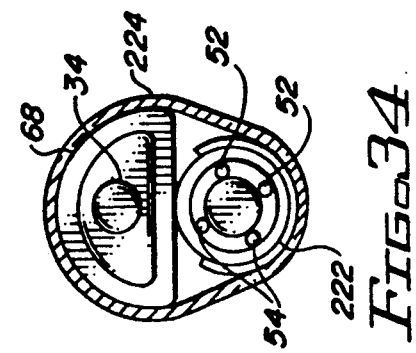

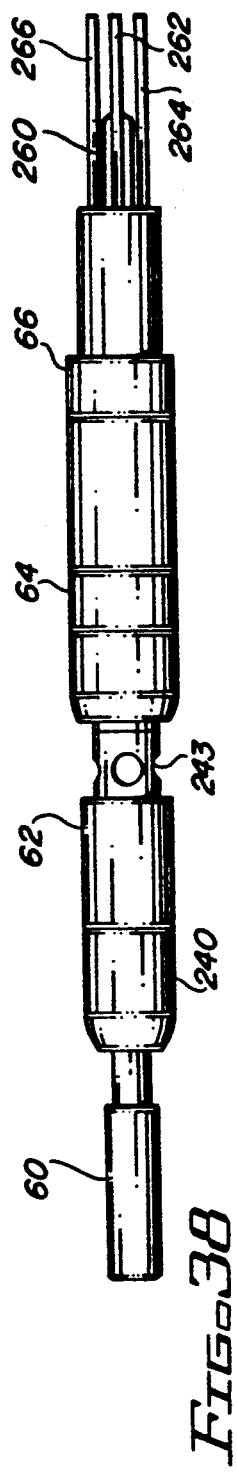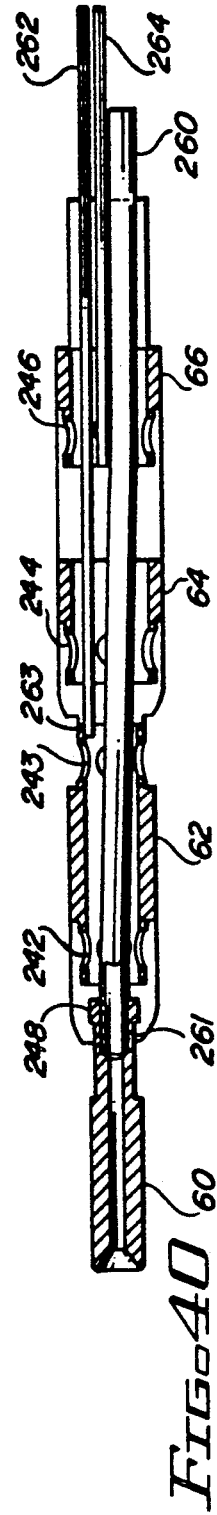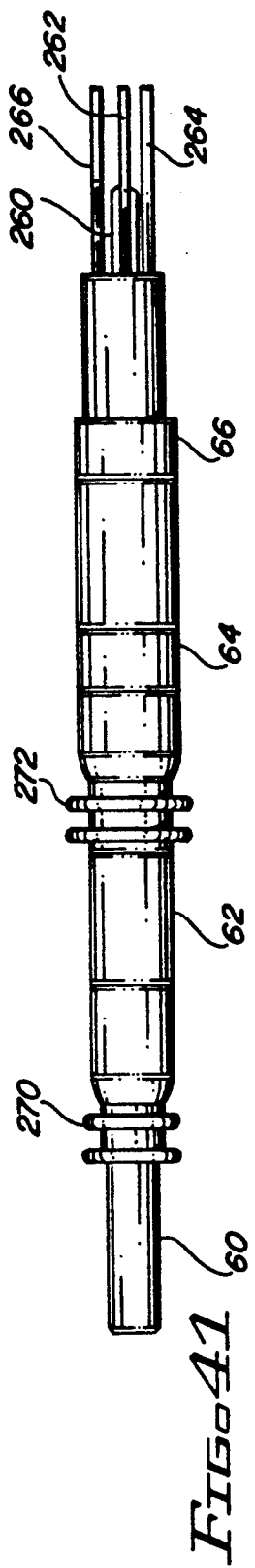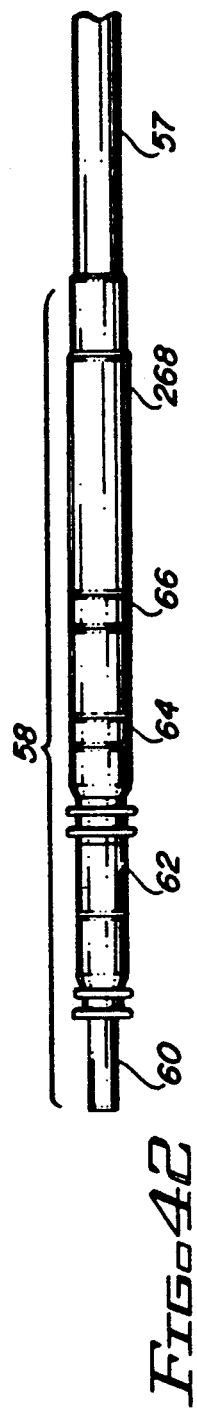

PACEMAKER LEAD FOR SENSING A PHYSIOLOGIC PARAMETER OF THE BODY

FIELD OF THE INVENTION

The present invention relates generally to implantable pacemaker leads, and more particularly, to an implantable pacemaker lead that can sense at least one physiologic parameter of the body such as oxygen saturation of the blood.

BACKGROUND

The evolution of the modern pacemaker lead may be best understood through a review of the development of the pacemaker itself. The earliest pacemaker simply delivered stimulation pulses at a fixed repetition rate. These were known as "asynchronous" or fixed rate pacemakers. "Unipolar stimulation" was achieved by delivering electrical pulses between the tip electrode of the lead and the pacemaker case. Due to their asynchronous nature, the stimulation pulse often competed with natural rhythms. The "demand" pacemaker included sense amplifiers to enable sensing of natural rhythms. In the presence of natural cardiac signals, the demand pacemaker would inhibit a stimulation pulse. In the absence of natural cardiac signals, the demand pacemaker would deliver stimulation pulses. However, sensing between the tip and the case (referred to as "unipolar sensing") sometimes detected myopotentials; that is, the electrical signals generated by the pectoral muscle tissue. The sensing of myopotentials can falsely inhibit the demand pacemaker.

To solve this problem, bipolar leads were developed. A bipolar lead has two electrodes located within the heart: a tip electrode and a ring electrode. The ring electrode is located approximately one-half inch proximally from the tip electrode. This configuration enabled a significant reduction of myopotential sensing, as well as eliminating any pectoral stimulation. However, depending on the orientation of the lead and the direction of the wavefront, bipolar sensing of cardiac signals would sometimes result in signals that are smaller than unipolar signals. The arrival of unipolar/bipolar programmability in demand pacemakers enabled the physician to noninvasively reprogram the pacemaker's polarity to accommodate the patient's changing conditions.

Modern pacemakers can now alter their stimulation rate to accommodate the patient's exercise or stress needs. These rate-responsive pacemakers employ a variety of sensors to determine the physiological condition of the patient. Physiologic sensors may be located on the pacemaker lead or within the pacemaker itself. Physiologic sensors in use today include: minute volume, temperature, oxygen saturation of the blood, respiration, stroke volume, ventricular gradient, activity, and pre-ejection period (PEP), etc.

The ideal physiologic sensor would be one that provides information about the patient's exercise level or workload, and ideally, will operate in a closed loop fashion. In other words, it should operate to minimize the divergence from the ideal operating point. For this reason, the development of a sensor for monitoring blood oxygen saturation for use with an implantable pacemaker is desirable. Oxygen saturation of the blood provides a direct indication of oxygen consumption of the patient during exercise. Furthermore, oxygen saturation has an inverse relationship with pacing rate. That is, as oxygen saturation decreases due to exercise, the pacing rate will increase so that the divergence from the optimum point is minimized.

The development of an oxygen saturation sensor and circuitry for operating such a sensor incorporated into a pacemaker lead is shown in several references. See, for example, U.S. Pat. No. 4,399,820, to Wirtzfeld et al.; U.S. Pat. No. 4,750,495, to Moore et al.; and U.S. Pat. No. 4,815,469, to Cohen et al.

Unfortunately, problems still exist which have heretofore hindered a widespread clinical use of such a pacing system. One of the major difficulties in developing an oxygen sensing system has been to develop a pacemaker lead having a reliable, hermetically enclosed sensor that can be located within the heart. The typical oxygen sensor in combination with a pacemaker lead includes one or more light-emitting diodes (LEDs), phototransistors and resistors. The prior art suffers from complex circuit designs, which designs are difficult to miniaturize and hermetically encapsule. Also, the process of providing a reliable weld to a relatively large area without damaging the sensor electronics is not an easy task.

Another problem is protecting the oxygen sensor circuitry from overvoltages, such as those seen during cardioversion, defibrillation and electrosurgery. In the event of a high voltage cardioversion or defibrillation pulse, the integrated circuits could be destroyed losing all rate-responsive functionality.

Another potential problem occurs when using one or both of the stimulation conductors as the sensor return conductor. Should the sensor fail or interfere with the stimulation electrodes' functionality, pacing of the heart may be jeopardized. For example, bodily fluids may intrude into the sensor circuitry or a lead fracture may occur at the sensor connection (particularly given the periodic forces that are regularly placed on the lead as it moves or flexes with the heart). Under these failure modes the stimulation electrodes could be impaired or even destroyed, thus losing all the functionality of the lead.

Another disadvantage of oxygen sensor designs that use the same conductors as for stimulating, is that they exhibit rectification of electrosurgery signals. Thus, the current oxygen sensor designs do not meet the proposed international Cenelac standard. Therefore, it is an objective of the present invention to provide a simple hermetic packaging technique for a physiological sensor in a pacemaker lead, particularly an oxygen saturation sensor.

It is an objective of the present invention to provide a packaging technique for a physiological sensor in a pacemaker lead that does not interfere with basic operation of the pacemaker.

It is an objective of the present invention to provide a physiological sensor in a pacemaker lead that is not affected by electrosurgery signals, a cardioversion pulse, or a defibrillation pulse.

It is an objective of the present invention to provide a physiological sensor in a pacemaker lead that permits either unipolar or bipolar stimulation.

It is further an objective of the present invention to provide a reliable sensor circuit with minimum components which will minimize the overall diameter of the lead.

Finally, it is also an objective that all of the aforesaid advantages and objectives be achieved without incurring any substantial relative disadvantage.

SUMMARY OF THE INVENTION

The disadvantages and limitations of the background art discussed above are overcome by the present invention. The present invention includes a body implantable lead having a proximal connector, a lead body having at least one conductor, and at least one stimulating electrode. In addition, the present invention includes two additional conductors, coupled to a hermetically sealed sensor, for sensing at least one physiologic parameter of the body. Advantageously, the conductors coupled to the sensor function independently from the stimulation conductors so that interference with basic operation of the pacemaker is prevented. Overvoltage protection circuitry for protecting the sensor circuitry is located within the pacemaker. Thus, the sensor is unaffected by electrosurgery signals, a cardioversion pulse, or a defibrillation pulse.

In the preferred embodiment, the lead body comprises a multi-lumen bipolar configuration, that is, a silicone or polyurethane tube with at least four lumens, or holes, therein. Each of the four conductors occupies one of the lumens.

In an alternate embodiment, the lead body comprises a "thin bipolar" configuration in which individual conductors are electrically isolated from each other by a thin electrically insulative, polymer coating. The conductors and the sensor assembly are further insulated by a layer of body compatible material.

In the preferred embodiment, the body implantable lead includes a sensor for sensing a specified characteristic of body fluid, such as the oxygen content of blood. In this configuration, a light-emitting source is used to transmit light through a transparent tubular housing to the body tissue. Light that is reflected back from the body due to the oxygen level of the blood is received by a light detector also located within the housing. To prevent light from impinging directly from the light-emitting source to the light detector, an insulating light barrier is disposed therebetween.

In the preferred embodiment, the housing is D-shaped and is preferably made of soda lime glass. The sensor components are mounted onto a microelectronic substrate which is advantageously placed on an inner flat portion of the D-shaped housing. End caps are used to seal the ends of the shell. Advantageously, each end cap has a glass frit sealing ring and a narrow bore for allowing one of the sensor terminals to pass therethrough. A hermetic seal is easily achieved by heating the glass frit such that the glass frit reflows between the shell and the end caps. Advantageously, the sensor terminals are sized to fit snugly within the narrow bore. The gap between the sensor terminals and the narrow bore is then sealed by localized welding, or otherwise sealing, the sensor terminals to the end cap.

In the preferred embodiment, at least one end cap includes an inner and an outer cap. The inner cap includes the glass frit sealing ring and a channel wide enough to slide the substrate therethrough. Advantageously, the inner cap and the end cap may be simultaneously refired in a firing oven to produce a superior hermetic seal. After the glass frit is fired, the substrate is slid through the wide channel of the inner cap onto the flat side of the D-shaped shell. The outer cap is sized to fit snugly within the inner cap and includes a narrow bore for allowing one of the sensor terminals to pass therethrough. After the substrate is in place, the outer cap is hermetically welded to the inner cap using localized welding. Thus, the sensor is reliably and hermetically sealed without damaging the delicate microelectronic circuits.

The D-shaped sensor assembly is placed on a carrier. The carrier may comprise a portion of a multi-lumen lead body which has a flat cavity therein for mounting the D-shaped sensor assembly thereon. In the preferred embodiment, the carrier is a separately molded part with lumens molded therein for making appropriate electrical contact between the lead body and the sensor.

Advantageously, the D-shaped housing reduces the area that needs to be hermetically sealed by more than half, and thus reduces the overall diameter of the lead. It is well known that small diameter leads are more easily introduced into the vein and easier and more flexible to position in the heart. Therefore, the overall diameter is a critical parameter in developing any new pacemaker lead.

It may therefore be seen that the present invention teaches a simple hermetic packaging technique for a physiologic sensor in a pacemaker lead, thus particularly enabling the production of an oxygen saturation sensor. In addition, the present invention provides a packaging technique for a physiologic sensor in a pacemaker lead that does not interfere with the basic operation of a pacemaker.

The present invention also provides a physiologic sensor in a pacemaker lead that is not affected by electrosurgery signals, a cardioversion pulse, or a defibrillation pulse. The pacemaker lead including the physiologic sensor of the present invention can be configured in either a unipolar or bipolar lead. In addition, the present invention also provides a reliable sensor circuit having the smallest number of components possible, which will minimize the overall diameter of the lead.

Finally, all of the aforesaid advantages and objectives are achieved without incurring any substantial relative disadvantage. It will therefore be perceived that the advantages of the present invention result in an implantable stimulation lead having a reliable hermetically sealed sensor that enables the use of a sophisticated, closed-loop, rate-responsive pacemaker. The present invention thereby enables a higher quality of life for the patient, making the present invention a highly desirable enhancement to implantable cardiac pacemaker therapy.

BRIEF DESCRIPTION OF THE DRAWINGS

Further features and advantages of the present invention may be more readily understood by reference to the following description taken in conjunction with the accompanying drawings, in which:

FIG. 3 shows a side view of the body implantable lead assembly of the present invention with the sensor mounted therein;

FIG. 4 shows an isometric view of the preferred housing of the present invention;

FIG. 5 shows a plan view of the housing shown in FIG. 4;

FIG. 6 shows an end view of the housing shown in FIG. 4;

FIG. 7 shows an profile view of the preferred end cap for the housing shown in FIG. 4;

FIG. 8 shows a cross-sectional view of the preferred end cap shown in FIG. 7;

FIG. 9 shows an isometric view of an alternate embodiment end cap which may be used instead of the end cap shown in FIG. 7;

FIG. 20 shows an isometric view of an alternate embodiment of the D-shaped sensor assembly, including the substrate placed within the housing with the end caps of the alternate embodiment shown in FIG. 9 attached thereto;

FIG. 21 shows a cross-sectional view of the assembly shown in FIG. 20;

FIG. 22 shows an isometric view of another alternate embodiment of the D-shaped sensor assembly, including the substrate placed within the housing with the end caps of the alternate embodiment shown in FIG. 11 attached thereto;

FIG. 23 shows a cross-sectional view of the assembly shown in FIG. 22;

FIG. 24 shows a cross-sectional view of the D-shaped sensor assembly of the preferred embodiment, including the substrate placed within the housing with at least one of the preferred end caps of FIG. 7 attached thereto;

FIG. 25 shows an end view of the preferred carrier used for mounting the D-shaped sensor;

FIG. 26 shows a plan view of the carrier shown in FIG. 25;

FIG. 27 shows a side view of the housing mounted onto the carrier of FIG. 25;

FIG. 28 shows an end view of the housing mounted onto the carrier of FIG. 25;

FIG. 29 shows an end view of the multi-lumen lead body;

FIG. 30 shows a partial cross-sectional view of the multi-lumen lead body in the area of the sensor;

FIG. 31 shows an isometric view of an alternate carrier;

FIG. 32 shows a cross-sectional side view of the housing mounted onto the alternate carrier of FIG. 31;

FIG. 33 shows a cross-sectional side view of the housing mounted on the "thin bipolar" lead body;

FIG. 34 shows an end view of the housing mounted onto the alternate carrier of FIG. 33;

FIG. 35 shows a first alternate embodiment for attaching the sensor housing onto the "thin bipolar" lead body;

FIG. 36 shows a second alternate embodiment for attaching the sensor housing onto the "thin bipolar" lead body;

FIG. 37 shows a third alternate embodiment for attaching the sensor housing onto the "thin bipolar" lead body;

FIG. 38 shows a profile view of a multi-polar connector subassembly for the lead;

FIG. 39 shows an end view of the multi-polar connector subassembly shown in FIG. 38;

FIG. 40 shows a cross-sectional profile view of a multi-polar connector subassembly shown in FIG. 38;

FIG. 41 shows a profile view of the multi-polar connector subassembly, including the sealing rings; and FIG. 42 shows a profile view of the multi-polar connector assembly, including the sealing rings and the protective sleeve.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Although the preferred embodiment of the present invention is directed towards the construction and hermetic sealing of an oxygen saturation sensor onto a pacemaker lead, the present invention is not limited to an oxygen saturation sensor. Any physiologic sensor that would be desirable to locate on a lead could be mounted by utilizing this method.

Figure 1:
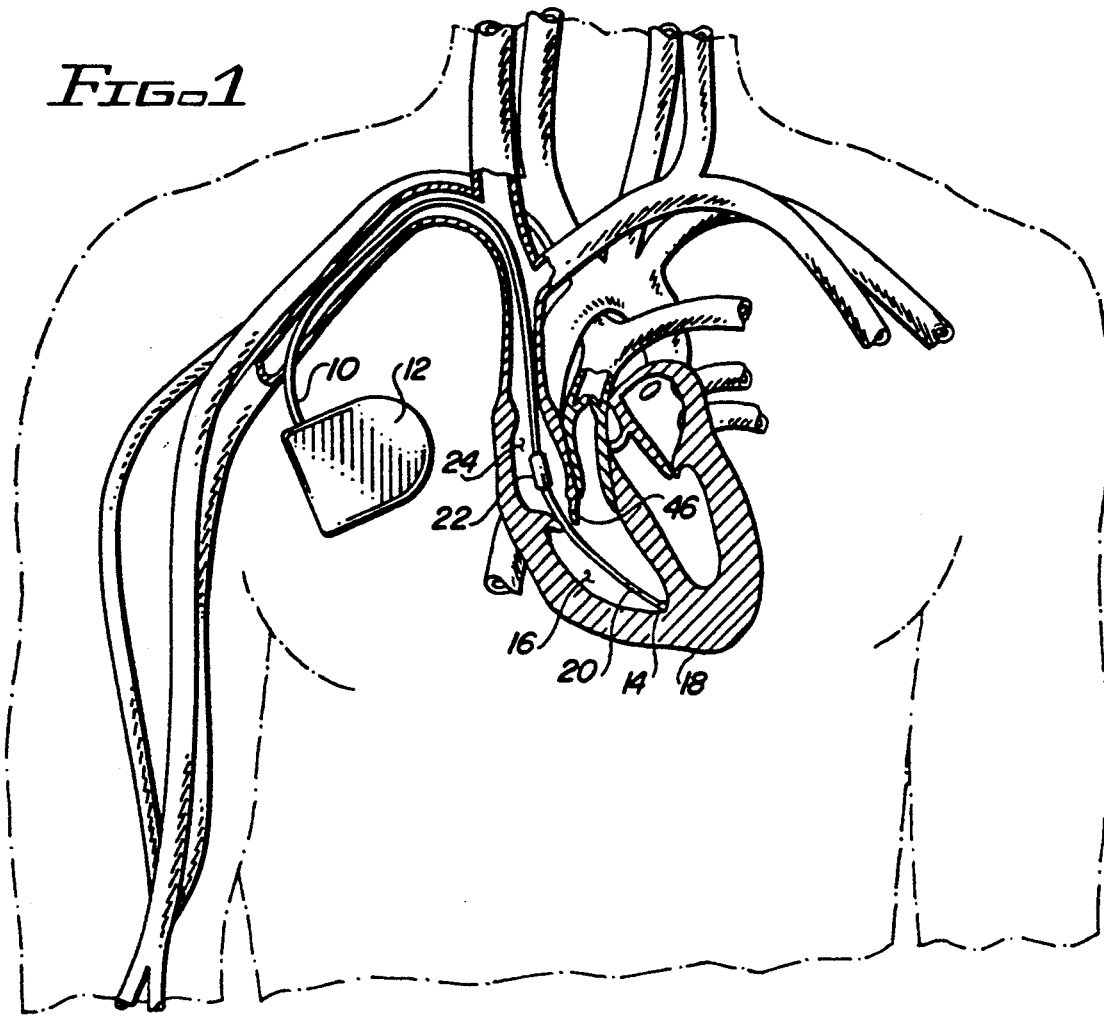
FIG. 1 is a diagrammatic illustration of the installation of the system of the present invention in the upper chest region of a human being.

Before describing the present invention in detail, it will be helpful to have a basic understanding of a rate-responsive pacemaker. In a typical application, a pacemaker lead 10 is connected to a rate-responsive pacemaker 12, as illustrated in FIG. 1. The rate-responsive pacemaker 12 is shown implanted in the right upper chest cavity. The pacemakers lead 10 is electrically and mechanically connected to the pacemaker 12. The pacemaker lead 10 is introduced into the heart 18 through a vein, with a distal tip electrode 14 of the pacemaker lead 10 being located in the right ventricle 16 of the heart 18.

The pacemaker lead 10 illustrated in FIG. 1 is shown connected to bipolar lead. Bipolar stimulation is achieved between the tip electrode 14 and a ring electrode 20 approximately one-half inch from the tip electrode 14. Although a bipolar lead is shown in the preferred embodiment, it is evident to one skilled in the art that a unipolar lead could also be used, if desired. In addition, the pacemaker 12 illustrated is a single-chamber pacemaker, although the principles of the present invention are equally applicable to both single and dual-chamber pacemakers.

An oxygen sensor 22 is positioned within an area of a living body where blood is able to come in contact with the light energy emitted by the oxygen sensor 22. The oxygen sensor 22 may be placed either within a vein that is carrying blood back to the heart 18, within the right atrium 24, or within the right ventricle 16 itself. In the preferred embodiment, the oxygen sensor 22 is positioned on the pacemaker lead 10 proximal to the ring electrode 20 so as to place the oxygen sensor 22 within the right atrium 24 of the heart 18. It is believed that sensing oxygen saturation of the blood within the right atrium is a more sensitive indicator of exercise. Further, when positioned properly within the heart 18, the pacemaker lead 10 is curved in a manner that causes the oxygen sensor 22 to face blood just prior to the blood's passage through the tricuspid valve 46 of the heart 18. For a complete discussion of the use of an oxygen sensor placed in the right atrium as the control mechanism for a rate-responsive pacemaker, see copending U.S. patent application No. 07/555,965, now U.S. Pat. No. 5,076,271 filed on Jul. 19, 1990, which is assigned to the assignee of the present invention. U.S. Pat. No. 5,076,271. filed on Jul. 19, 1990, is hereby incorporated herein by reference.

Figure 2:
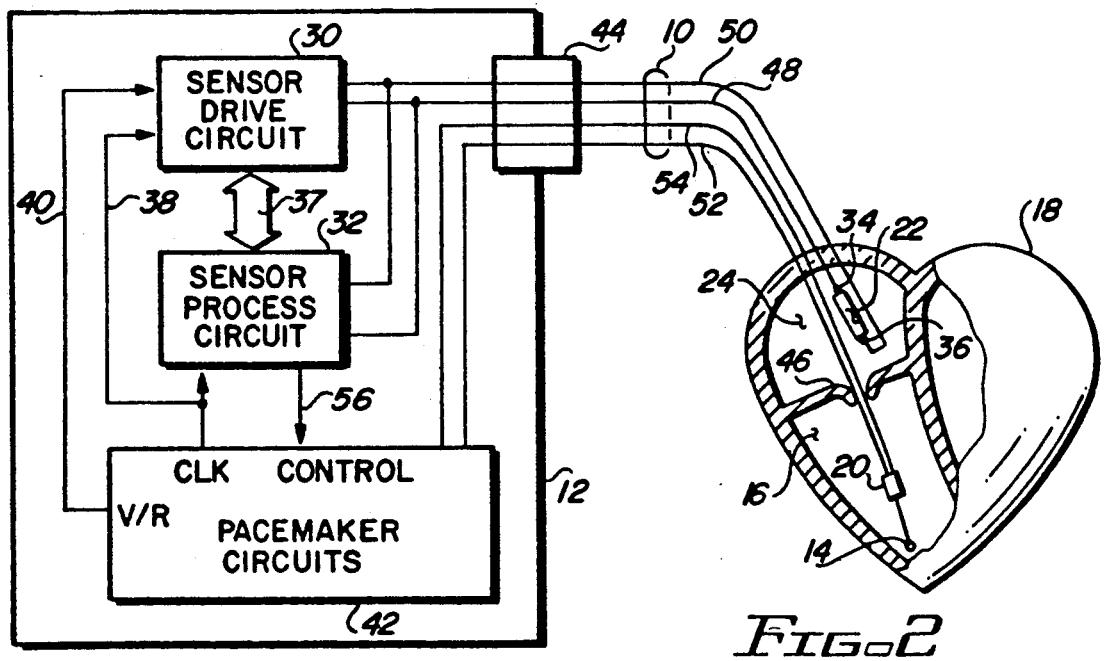
FIG. 2 is a schematic block diagram of a pacemaker system incorporating the oxygen sensor of the present invention.

In FIG. 2, a block diagram is shown illustrating the manner in which the oxygen sensor 22 is connected to control circuitry within the pacemaker 12. Within the pacemaker 12, a sensor drive circuit 30 provides the current pulse used to drive the oxygen sensor 22. Similarly, a sensor process circuit 32 monitors the voltage developed across the sensor terminals 34, 36. Appropriate timing signals 37 are shared between the sensor drive circuit 30 and the sensor process circuit 32. Further, in order to synchronize the sensing function of the oxygen sensor 22 with other events, the sensor drive circuit 30 and the sensor process circuit 32 typically receive timing signals from the pacemaker circuits 42. Timing signals include at least a clock signal 38 and a timing reference (V/R) signal 40 (signifying either that V-stimulation pulse or an R-wave has occurred).

The sensor process circuit 32 shown in FIG. 2 develops a control signal 56 that is representative of the reflectance properties of the blood (and hence relatable to the amount of oxygen that has been sensed within the blood). The control signal 56 is used to control the rate at which the pacemaker 12 delivers a stimulation pulse to the heart 18. Thus, the system shown in FIG. 2 is representative of a rate-responsive pacemaker 12 wherein the pacemaker rate varies as a function of the sensed oxygen content of the blood.

In the preferred embodiment shown in FIG. 3, the pacemaker lead 10 is a bipolar lead. The pacemaker lead 10 includes a lead body 57 having four conductors 48, 50, 52, 54 (FIG. 2) therein. The pacemaker lead 10 further includes a multi-polar connector assembly 58 which is designed to mate with the pacemaker 12 by way of a multi-polar pacemaker electrode connector 44 (FIG. 2). Thus, the multi-polar connector assembly 58 includes four electrical contacts 60, 62, 64 and 66. The electrical contact 60 is connected to the tip electrode 14. The electrical contact 62 is connected to the ring electrode 20. The electrical contacts 64, 66 are connected to a first and second sensor terminal 34, 36, respectively. In a unipolar lead body configuration, a tripolar electrode connector would be employed, thus eliminating the need for contact 62 for the ring electrode 20. In the preferred embodiment, the sensor 22 is combined with the bipolar lead in the area of 59. As is known in the art, sensing cardiac events occurs using the same electrodes as for stimulation. Advantageously, both terminals 34, 36 of the oxygen sensor 22 are connected to separate conductors 48, 50, respectively, of the pacemaker lead 10, which are electrically independent of the conductors 52, 54 which are used for stimulation.

It is believed that the best way of describing the present invention is to describe the apparatus at the lowest level of assembly and then to describe the construction of the body implantable lead. FIG. 4 shows a tubular shell 68 which is used for housing the sensor electronics. A plan view and a cross-sectional view of the shell 68 may be seen in FIGS. 5 and 6, respectively. The shell 68 may be made of any hermetic material, such as stainless steel, ceramic, glass, etc. For an oxygen saturation sensor, the shell 68 should be a transparent material, such as glass, and more particularly, in the preferred embodiment it is soda lime glass. In the preferred embodiment, the shape of the shell 68 is "D-shaped."

In the preferred embodiment, the thickness of the shell 68 is approximately 0.010 inch, the inner radius is approximately 0.035 inch, with the outer radius therefore being approximately 0.045 inch. This leaves a flat surface 69 on the inside of the shell 68 onto which may be located a microelectronic substrate (not shown). This configuration is ideal since it minimizes the overall diameter of the sensor. The length of the shell 68 is dictated by the size of the microelectronic substrate, which in turn is dictated by the number of components.

In FIGS. 7 and 8 is the preferred embodiment of an end cap 70 that may be used to seal the shell 68. The end cap 70 has an inner cap 72 and an outer cap 82. As seen in FIG. 8, the inner cap 72 comprises a tubular section of metal, preferably 90 percent Platinum and 10 percent Iridium, having a channel 76 therethrough. At one end, the inner cap 72 has a preformed glass frit sealing ring 78. At the other end, the inner cap 72 has a protruding lip 80.

The outer cap 82 also comprises a tubular section of metal, preferably made of a material which is 90 percent Platinum and 10 percent Iridium, having a channel 86 therethrough. At one end, the outer cap 82 has a protruding lip 90. The outer diameter of the protruding lip 90 is dimensioned so as to have a snug fit within the protruding lip 80 of the inner cap 72. Adjacent to the protruding lip 90 is a protruding shoulder 92. When mated with the inner cap 72, the protruding shoulder 92 butts up against the protruding lip 80 of the inner cap 72. At the same end, the width of the channel 86 is dimensioned so as to be able to accommodate conductive wires which may be slightly curved without touching the outer cap 82. At the other end of the outer cap 82, the channel 86 has a narrow portion 94. The narrow portion 94 of the channel 86 is dimensioned so as to have a snug fit about a conductive wire (not shown) which will form one of the sensor output terminals. In FIG. 7, the outer cap 82 is shown to have threads 98 to facilitate attachment of the sensor conductors 48, 50.

Figure 10:
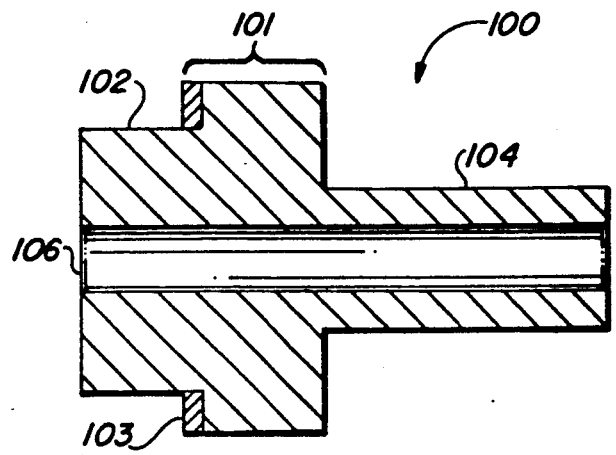
FIG. 10 shows a cross-sectional view of the end cap shown in FIG. 9.

In FIGS. 9 and 10, an alternate embodiment of an end cap that may be used to seal the shell 68 is shown. An end cap 100 has a center portion 101 having an outer radius and shape substantially identical to the outer radius and shape of the shell 68. The end cap 100 may be made of metal, and is preferably made of a material which is 90 per cent Platinum and 10 percent Iridium. The end cap 100 has on one end a protruding portion 102 which has an outer radius and shape substantially identical to the inner radius and shape of the shell 68. The end cap 100 also has a preformed glass frit sealing ring 103. On the other end of the end cap 100 is a tubular portion 104. Each end cap 100 has a bore 106 therethrough to permit passage of a conductive wire (not shown) which will form one of the sensor output terminals. The purpose of the tubular portion 104 will be explained below in the description of the hermetic sealing.

Figure 11:
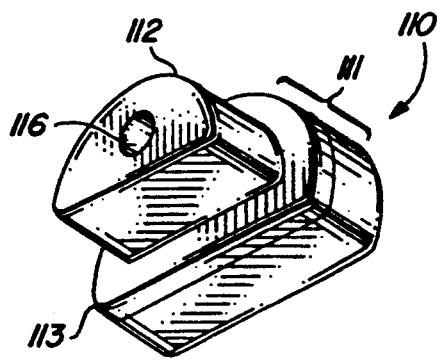
FIG. 11 shows an isometric view of an alternate embodiment end cap which may be used instead of the end cap shown in FIG. 7.
Figure 12:
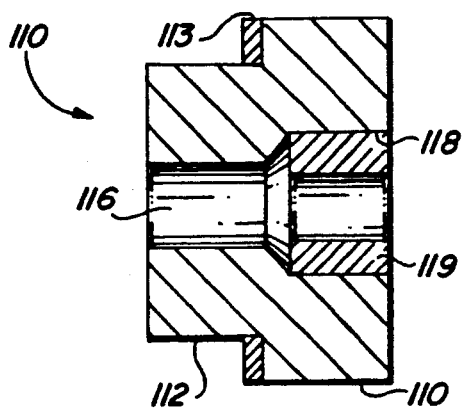
FIG. 12 shows a cross-sectional view of the end cap shown in FIG. 11.

In FIGS. 11 and 12, an alternate embodiment of an end cap that may be used to seal the shell 68 is shown. An end cap 110 has a portion 111 having an outer radius and shape substantially identical to the outer radius and shape of the shell 68. The end cap 110 has on one end a protruding portion 112 which has an outer radius and shape substantially identical to the inner radius and shape of the shell 68. The end cap 110 also has a preformed glass frit sealing ring 113. Each end cap 110 has a bore 116 therethrough with a larger counterbore 118 at one end to permit passage of a sensor terminal. As shown in FIG. 12, glass frit 119 is preformed within the counterbore 118, the purpose of which will be explained below in the description of the hermetic sealing.

A complete description of the sensor electronics of the preferred embodiment of an oxygen sensor 22 may be found in copending U.S. patent application No. 07/403,208, now U.S. Pat. No. 5,040,538 filed on Sep. 5, 1989, which patent application is assigned to the assignee of the present invention. U.S. Pat. No. 5,040,538 is hereby incorporated by reference. For convenience, the most pertinent figure of the application is reproduced herein as FIG. 13. Although the present invention is discussed specifically with the incorporation of U.S. Pat. No. 5,040,538, the invention is believed equally applicable to other circuit configurations for an oxygen saturation sensor.

Briefly, the sensor electronics includes a light source and a light receiver. In the preferred embodiment shown in FIG. 13, the light source is a single LED 120. The light receiver comprises a NPN-type phototransistor 122 which drives an integrator capacitor 124. (In practice, the integrator capacitor 124 is the parasitic capacitance of the phototransistor 122 and a PNP-type transistor 125.) The LED 120 is driven by the sensor drive circuit 30 located in the pacemaker 12. Light 126 which is emitted from the LED 120 is directed outside the oxygen sensor 22 onto the blood. A portion of light 127 is reflected back towards the oxygen sensor 22 onto the phototransistor 122.

The integrator capacitor 124 begins to integrate the signal from the phototransistor 122 as soon as the LED 120 is fully turned on. Two resistors 130, 132 serve to bias the NPN-type phototransistor 122 and the PNP-type transistor 125. When the output of the integrator capacitor 124 exceeds the base-emitter junction of the PNP-type transistor 125, the transistor 125 will conduct. The conducting PNP-type transistor 125, in series with the NPN-type phototransistor 122, forms a latch. The latch, connected across the LED 120, will clamp the voltage across the LED 120 causing the voltage to drop. The difference between the time when the LED 120 is fully turned and the time when the voltage across the LED 120 drops, is then determined. The oxygen content of the blood is inversely related to the measured time interval. Thus, the blood oxygen content is determined by merely monitoring the voltage across the LED 120.

Figure 13:
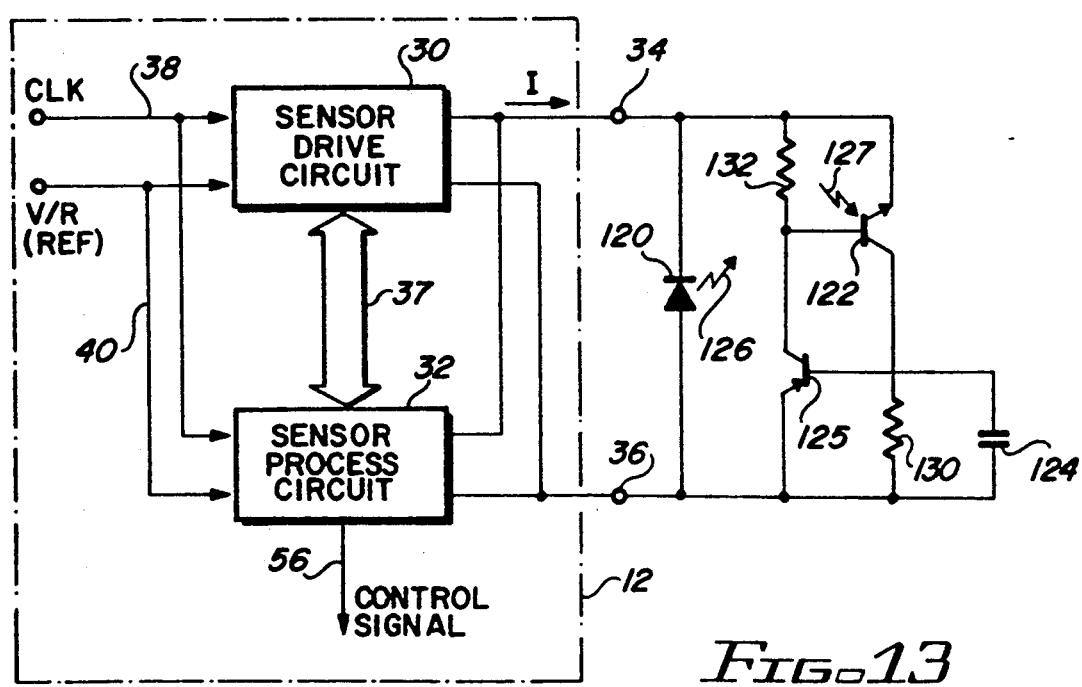
FIG. 13 is a schematic block diagram showing one possible electrical design for the oxygen sensor of the present invention in conjunction with the portion of the pacemaker system operating the oxygen sensor.
Figure 14:
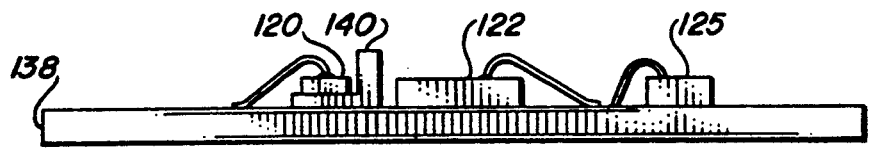
FIG. 14 shows a side view of the substrate and some of the electrical components shown in FIG. 13.
Figure 15:
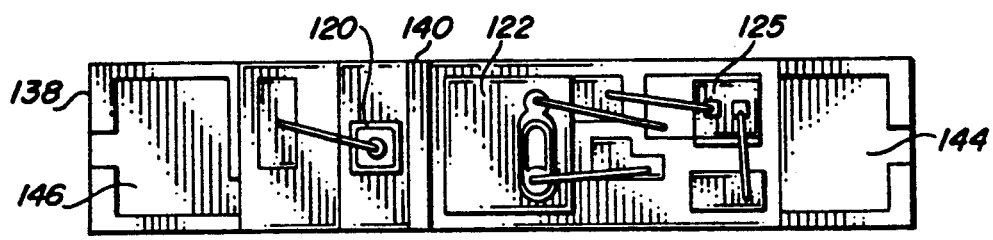
FIG. 15 shows a composite top view of the substrate shown in FIG. 14, including the integrated circuit components shown in FIG. 13.
Figure 16:
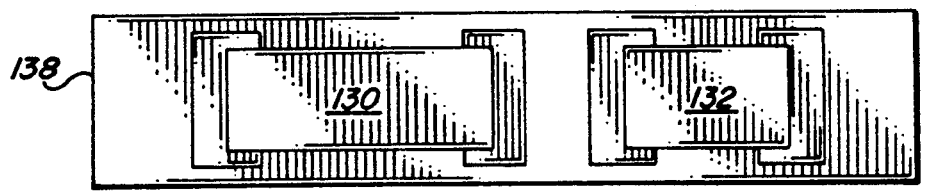
FIG. 16 shows a composite bottom view of the substrate shown in FIG. 14, including the screen printed resistors shown in FIG. 13.

FIGS. 14–16 show a side, top and bottom view, respectively, of a microelectronic substrate 138 incorporating the electrical schematic of FIG. 13. Suffice it to say that the microelectronic substrate 138 is made in accordance with conventional thick film technology materials and construction. Briefly, the substrate 138 has multiple layers of metallization screen printed thereon, each layer being isolated by each other using a screen printed dielectric material. As shown in FIG. 15, the LED 120, the phototransistor 122 and the transistor 125 are attached on the top side of the substrate 138. As shown in FIG. 16, the resistors 130, 132 are screen printed on the bottom side of the substrate 138. Interconnections between each layer are made with vias. In composite top view of the substrate shown in FIG. 15, bonding areas 144 and 146 provide a large area to attach conductive wires (not shown) which will form the sensor terminals 34, 36 (FIG. 2), respectively.

Figure 17:
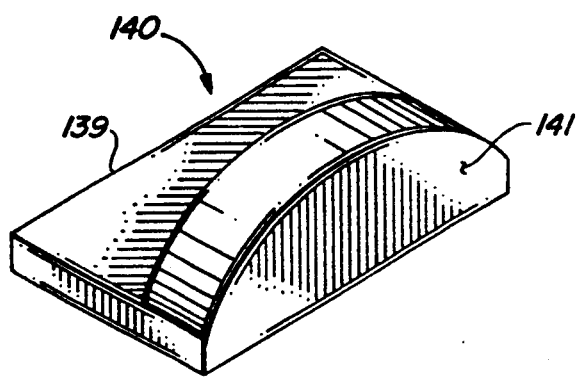
FIG. 17 is an isometric view of the L-shaped barrier.
Figure 18:
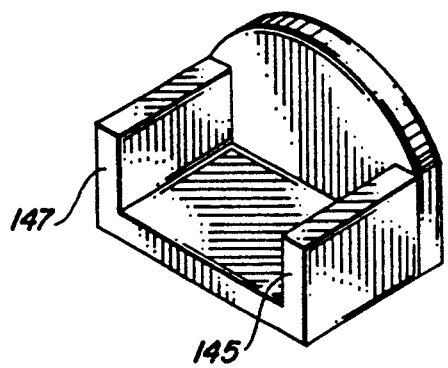
FIG. 18 is an isometric view of the chair-shaped barrier.

In the preferred embodiment, the LED 120 is separated from the phototransistor 122 by a barrier 140 (FIG. 14) to prevent light from the LED 120 directly impinging onto the phototransistor 122. Ideally, the light source should be as close as possible to the light receiver to reduce losses and to enhance coupling. In the preferred embodiment (shown in FIG. 17), the barrier 140 is made of a very thin L-shaped piece of metal, having a flat side 139 and a curved side 141 perpendicular to the flat side 139. The anode of the LED 120 is electrically and mechanically attached to the flat side 139 of the L-shaped barrier 140. The flat side 139 of the barrier 140 is then electrically and mechanically mounted onto the substrate next to the phototransistor 122. The curved side 141 of the L-shaped barrier 140 has a radius equal to the inner radius of the D-shaped shell 68 to completely block light from the LED 120 from impinging onto the phototransistor 122. Advantageously, the pre-attachment of the LED 120 onto the L-shaped barrier 140 significantly improves manufacturability. In an alternate embodiment, a chair-shaped barrier 143 may be used instead of the L-shaped barrier 140, as shown in FIG. 18. The chair-shaped barrier 143 has the added advantage of improved reflective properties by having arms 145, 147 which serve to direct the light 126 from the LED 120 towards the body.

It can therefore be appreciated that the physical layout of the substrate 138 shown in FIGS. 14–16 is but one designer's implementation and that numerous possible layout designs are readily apparent to one skilled in the art. Advantageously, the number and types of components chosen have greatly simplified the substrate design and enabled a relatively small size substrate, approximately 0.050×0.340 inches.

Figure 19:
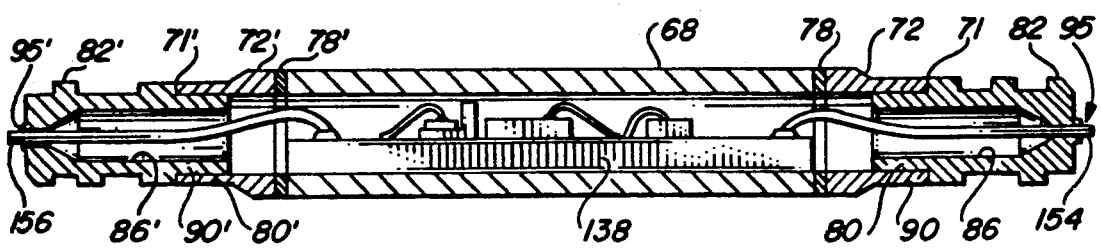
FIG. 19 shows a cross-sectional view of the D-shaped sensor assembly of one embodiment, including the substrate placed within the housing with the preferred end caps of FIG. 7 attached thereto.

FIG. 19 shows one embodiment of the sensor assembly using the preferred end cap 70 (shown in FIG. 7). Since two identical end caps are employed, for readability purposes, complimentary elements will be referred to as primed, e.g., inner caps 72 and 72'. The substrate 138 is shown placed on the flat inside surface of the shell 68. Conductive wires 154, 156, are prewelded to the ends of the substrate 138 by way of conductive bonding pads 144, 146 (FIG. 15), respectively, to form the sensor terminals 34, 36 (FIG. 2). In the preferred embodiment, the conductive wires 154, 156 are made of 0.005 inch gold wire and either epoxied or gap welded onto the bonding pads 144, 146.

In the embodiment shown in FIG. 19, a hermetic seal is achieved as follows. First, the inner caps 72, 72' and the D-shaped shell 68 are hermetically sealed by reflowing the glass frit sealing rings 78, 78'. A hermetic seal has been achieved using a firing oven at about 500 degrees Celsius for approximately 30 minutes, but other combinations of time and temperature may be possible. Although a firing oven is the preferred method of reflowing the glass frit sealing rings to the housing, alternate methods of localized heating, such as laser welding and resistive heating, are possible. The substrate 138, with preattached conductive wires 154, 156, is then inserted into the shell 68. Next, the outer caps 82, 82' are received within the inner caps 72, 72'. The conductive wires 154, 156, extend through the narrow portions 94, 94' of the channels 86, 86', respectively. The inner caps 72, 72' and the outer caps 82, 82' are hermetically sealed by localized welding circumferentially at 71, 71'. In the preferred embodiment this is achieved using laser welding. Finally, the conductive wires 154, 156, are hermetically sealed by circumferentially welding at 95, 95' of the outer caps 82, 82'.

Advantageously, the reflowing of the glass frit is performed before the substrate is inserted within the housing, thus, eliminating the possibility of damaging the delicate circuits. The localized welding of the inner cap 72 to the outer cap 82 is also designed to have negligible effect on the sensor circuits. Since the outer cap 82 acts like a heat sink, the localized welding at the narrow portion 94 of the channel 86 has minimal effect on the sensor circuits.

In an alternate embodiment shown in FIG. 20, the substrate 138, with pre-attached conductive wires 154, 156, is place on the flat surface inside the shell 68. The end caps 100, 100' may be inserted into the ends of the shell 68 such that the conductive wires 154, 156 pass through the bores 106, 106', respectively. A hermetic seal may be achieved by reflowing the glass frit sealing rings 103, 103' using resistance heating at about 325 degrees Celsius for approximately 1 minute. This resistance heat weld process permits a hermetic seal while preventing excessive heat from damaging the delicate microelectronic circuits. In the alternate embodiment shown in FIG. 20, the tubular portions 104, 104' of the end caps 100, 100' may be crimped against the conductive wires 154, 156, respectively. The conductive wires 154, 156 may then be laser or gap welded to hermetically seal the remaining opening.

In the other alternate embodiment shown in FIGS. 22 and 23, the substrate 138, with pre-attached conductive wires 154, 156, is also placed on the flat surface inside the shell 68. The end caps 110, 110' may be inserted into the ends of the shell 68 such that the conductive wires 154, 156 pass through the bores 116, 116', respectively. A hermetic seal may be achieved by reflowing the glass frit sealing rings 113, 113', 119, 119' using resistance heating at about 350 degrees Celsius for approximately one minute.

In the embodiments shown in FIGS. 20-23, the conductive wires 154, 156 could be made of platinum wire which are hammered flat at one end thereof to provide a large surface area for welding. To facilitate a good weld bond for the conductive wires 154, 156 a metal alloy tab (not shown) may be first attached to the substrate 138 prior to welding the conductive wires 154, 156. This configuration may provide improved mechanical strength and ease handling operations.

In the preferred embodiment shown in FIG. 24, a first end cap 73 is used at one end of the shell 68. The end cap 73 is a single piece, similar to the embodiments shown in FIGS. 20-23. At the other end of the shell 68, the preferred embodiment uses the inner cap 72 and the outer cap 82 cap shown in FIGS. 7 and 8. The inner cap 72 is fired as described above to form a hermetic seal with the shell 68. The end cap 73 has a sealing ring 75 which may be refired simultaneously with the sealing ring 78 of the inner cap 72. The substrate is then slid into the open channel 76 and placed on the flat inside surface of the shell 68. The outer cap 82 is then attached as described above. Advantageously, this configuration eliminates one weld step from the hermetic sealing process.

In the preferred embodiment shown in FIGS. 25 and 26, a multi-lumen carrier 160 is used for mounting the shell 68 thereon. Preferably, the carrier 160 is D-shaped and complimentary in size to the D-shaped sensor 22 (FIG. 28). The carrier 160 has three lumens 162, 164, 166 for inserting conductors 172, 174, and 176, respectively, therein. Conductor 172 is made of a conductive tube so that a guidewire (not shown) may be inserted therethrough. (Guidewires are used only during the placement of the electrode tip to provide extra stiffness in the lead.) Thus, the lumen 162 must be larger than the lumens 164 and 166. To further ensure that the conductors 172, 174, and 176, do not short to each other they are insulated by a thin polyimide tube (not shown). The outer flat side of the D-shaped sensor 22 is then place against a flat side 168 of the carrier 160, as best seen in FIG. 28.

In the preferred embodiment, the carrier 160 is made of epoxy and is cast (together with the conductors 172, 174, 176) onto the D-shaped shell 68. Once cast, the shell 68 and the carrier 160 are encased in a thin layer of polyurethane cover tubing 178, or other transparent body compatible material that will not obscure the optical window. Suitable materials include the polyurethane material sold under the trademark PELLATHANE and manufactured by Dow, or an elastomer material manufactured by Dow Corning, such as Elastomer #Q7-4765, or equivalent type of silicone rubber.

The shell 68, now attached to the carrier 160, is spliced between two identical pieces of the lead body 57 as shown in FIG. 30. The lead body 57 insulates the conductors 48, 50, 52 and 54 from each other in a multi-lumen tubing made of body compatible material. For readability purposes, the complimentary elements of the distal portion of the lead body 57 will be referred to as primed, e.g., lead body 57'. In the preferred embodiment, as shown in FIGS. 29 and 30, the lead body 57, 57' is made of a multi-lumen tubing. As shown in FIG. 29, the multi-lumen lead body 57 of the preferred bipolar configuration requires four lumens, or holes, 182, 184, 186, 188 within a tube of body compatible material. The lumen 182 for the stimulating conductor 52 is larger than the other lumens due to the need to also pass a guidewire, which is used to position the lead into the heart.

In the area of 175, shown in FIG. 30, the conductor 172 is spot-welded or otherwise connected to conductor 52' which in turn is connected to the tip electrode 14. The conductor 174 is spot-welded or otherwise connected to conductor 54' which is connected to the ring electrode 20. The conductor 176 for the sensor 22 is laser welded or otherwise connected to the outer cap 82'.

In the area of 177, the conductor 172 is spot-welded or otherwise connected to conductor 52 which in turn is connected to the electrical contact 60 (FIG. 3). The conductor 174 is spot-welded or otherwise connected to the conductor 54 which is connected to the electrical contact 62 (FIG. 3). The conductor 176 for the sensor 22 is laser welded or otherwise connected to conductor 50 (not shown) which is connected to electrical contact 64 (FIG. 3). The outer cap 82 is electrically connected to conductor 48 and to electrical contact 66 (FIG. 3).

The shell 68, the carrier 160, and a small portion of the lead body 57, 57' are then covered by silicone rubber splice tubing 191. Medical adhesive is used to fill any gaps between the lead body 57, 57', the carrier 160, and the shell 68. A window 193 in the silicone rubber splice tubing 191, located over the light source and the light receiver, helps to minimize light losses.

In an alternate embodiment, shown in FIG. 31, an alternate carrier 190 is shown. The carrier 190 is a modified piece of multi-lumen tubing having four lumens, or holes, 192, 194, 196, 198 therein. The substrate 138 is placed on the flat portion 200 of the carrier 190 so that the overall diameter is equal to the diameter of the lead 10. As shown in FIG. 32, conductors 202, 204, and 206 are inserted into the lumens 192, 194, 196, respectively. Electrical connection between the conductors 202, 204, and 206 and the conductors 48, 50, 52, and 54 are made in a similar fashion as described above in conjunction with FIG. 30.

In an alternate embodiment shown in FIGS. 33 and 34, the lead 10 comprises a "thin bipolar" configuration. "Thin bipolar" is used herein to refer to a coaxial bipolar lead wherein individual filars are electrically insulated from each by a thin polymer insulative coating and then coaxially wound together. The insulative coating may be the polymer materials sold under the trademarks TEFLON and TEFZEL, manufactured by DuPont, which materials have good electrical insulating properties without adding significant bulk. Each conductor 48, 50, 52, 54 (FIG. 2) is comprised of two filars for redundancy. The coiled filars which make up the stimulating conductors 52 and 54 are insulated by a layer of body compatible material to form an inner lead body 222 (FIG. 34). The filars which make up the sensor conductors 48 and 50 are coiled about the inner lead body 222 and spot-welded to the sensor terminals 34 and 36, respectively (FIG. 33).

In the "thin bipolar" configuration, the shell 68 may be mounted onto the inner lead body 222 proximal to the ring electrode 20. The shell 68 and the sensor conductors 48, 50 are then insulated by an insulating layer 224 to complete the lead 10. Advantageously, no additional electrical isolation which would otherwise increase the bulk of the diameter of the lead is necessary, thereby reducing the overall size of the lead.

In FIGS. 35 through 37, three methods of mounting the shell 68 onto the "thin bipolar" lead 10 are shown. In FIG. 35, a semi-circular mounting clip 230 is shown which snaps onto the inner lead body 222 (FIG. 33) and holds the shell 68 firmly in place for potting. In FIG. 36, a circular mounting ring 232 is designed such that the inner lead body 222 (FIG. 33) may pass through the mounting ring 232. One or two mounting rings 232 may be employed to hold the shell 68 firmly in place. In FIG. 37, angular projections or mounting shoulders 234 extending from the shell 68 are shown which would clip onto the inner lead body 222 (FIG. 33). Alternately, the shell 68 may be held in place by appropriate tooling and simply potting it onto the inner lead body 222.

FIGS. 38-42 show one possible configuration of a multi-polar connector assembly 58 for the lead 10. FIG. 38 shows the four spaced apart electrical contacts 60, 62, 64 and 66 which are injection molded in a body compatible material 240. Suitable materials include the polyurethane material sold under the trademark PELLATHANE and manufactured by Dow, or an elastomer material manufactured by Dow Corning, such as Elastomer #Q7-4765, or equivalent type of silicone rubber. To improve the mechanical strength and the bonding between the body compatible material and the electrical contacts, circular holes 242, 243, 244 and 246 (FIG. 40) are formed within the electrical contacts 62, 64 and 66 enabling the body compatible material to "lock" into the electrical contacts 62, 64 and 66. Electrical contact 60 has a "dog bone" shape at one end 248 which also helps the body compatible material to "lock" into the electrical contact 60.

As seen in the end view (FIG. 39), there are four conductors 260, 262, 264 and 266 which are also injection molded in the body compatible material 240. The conductor 260 is a conductive tube so that a guidewire (not shown) may pass therethrough. The proximal end of the conductor 260 is connected to the electrical contact 60 at location 261, as shown in the cross-sectional view of FIG. 40. The conductor 262 is connected at the proximal end to the electrical contact 62 at location 263. The conductor 264 is connected at the proximal end to the electrical contact 64 (not shown). The conductor 266 (FIG. 38) is connected at the proximal end to the electrical contact 66 (not shown). Advantageously, conductors 262, 264 and 266 are straight wires (i.e., not coiled) made of a noncorroding metal, preferably MP35N stainless steel, having a diameter of 0.012 inch. This configuration thereby eliminates unnecessary bulk in the multi-polar connector assembly 58.

Injection molded seal rings 270, 272 shown in FIG. 41 are used to prevent bodily fluids from creating a low impedance between the tip electrode 14, the ring electrode 20 and sensor terminal 34. The seal rings 270 and 272 are either stretched and slid into place or they may be expanded by soaking them in a solvent such as isopropyl alcohol or the material sold under the trademark FREON and manufactured by Dupont. Alternately, the seal rings 270, 272 may be injection molded together with the electrical contacts 60, 62, 64 and 66. Seal rings could also be placed between electrical contacts 64 and 66, and between electrical contact 66 and the body. However, in the preferred embodiment, these seal rings are located within the multi-polar pacemaker electrode connector 44 itself.

The distal end of the conductor 260 is welded to conductor 52 (FIG. 2) corresponding to tip electrode 14. The distal ends of the conductors 262, 264 and 266 are spliced to conductors 54, 48 and 50 (FIG. 2), respectively, corresponding to the ring electrode 20 and the sensor terminals 34 and 36 (FIG. 2). Medical adhesive is used to insulate the spliced area, including the distal end of conductive tube 260. Before the medical adhesive cures, a protective sleeve 268 (FIG. 42) is slid over the spliced area.

Advantageously, it can be seen that the present invention teaches a simple hermetic packaging technique for a physiologic sensor in a pacemaker lead, thus particularly enabling the production of an oxygen saturation sensor. In addition, by using four conductors rather than the two conductors of the prior art, a defibrillation pulse or a cardioversion pulse will not damage the delicate sensor electronics. Furthermore, high frequency protection circuitry currently employed within the pacemaker may be coupled to the sensor to further protect the sensor's integrated circuits, thereby providing a pacing system with can meet the proposed Cenelac standards without adding extra circuitry to the sensor.

It will therefore be perceived that the advantages of the present invention result in an implantable stimulation lead having a reliably hermetically sealed sensor which enables the use of sophisticated, closed-loop, rate-responsive pacemaker, enabling a higher quality of life for the patient, thus making the present invention a highly desirable enhancement to implantable cardiac pacemaker therapy.

What is claimed is:

1. A body implantable lead, the lead including a plurality of electrode terminals at a proximal end, at least one stimulating electrode delivering stimulation pulses at a distal end, and a first conductive means for electrically connecting the stimulating electrode to one of the plurality of electrode terminals, the implantable lead comprising:

sensing means for sensing a specified characteristic of the body, the sensing means having a proximal and a distal sensor terminal;

a tubular D-shaped shell having a flat surface with the sensing means mounted thereon, the shell having two open ends;

two end caps dimensioned to fit into the two open ends of the shell, respectively, each end cap having a channel therethrough, allowing one of the sensor terminals to pass therethrough;

means for hermetically sealing the end caps to the shell;

a carrier having a flat side mounting the D-shaped shell thereon, the carrier further having at least a first and second lumen therethrough, wherein the first conductive means passes through the first lumen in the carrier;

a second conductive means for electrically connecting another one of the plurality of proximal electrode terminals to the distal sensor terminal, the second conductive means passing through the second lumen in the carrier;

a third conductive means for electrically connecting another one of the plurality of proximal electrode terminals to the proximal sensor terminal; and means for insulating the first, second, and third conductive means for each other.

2. The body implantable lead, as recited in claim 1, wherein the carrier is a multi-lumen tube having a recess therein, the recess having a flat surface mounting the sensing means thereon.

3. The body implantable lead, as recited in claim 1, wherein:

the implantable lead includes a ring electrode and a fourth conductive means electrically connected between the ring electrode and another one of the plurality of electrode connectors;

the carrier includes a third lumen passing the fourth conductive means therethrough; and the insulating means further includes means for insulating the fourth conductive means from the first, second, and third conductive means.

4. The body implantable lead, as recited in claim 1, wherein the insulating means is a multi-lumen lead body made of body compatible material.

5. The body implantable lead, as recited in claim 3, wherein the insulating means comprises a thin polymer coating about the first, second, third and fourth conductive means.

* * * * *